United States Patent [19]

Nishioka

[11] 4,403,273
[45] Sep. 6, 1983

[54] ILLUMINATING SYSTEM FOR ENDOSCOPES

[75] Inventor: Kimihiko Nishioka, Hachiouji, Japan

[73] Assignee: Olympus Optical Co., Ltd., Tokyo, Japan

[21] Appl. No.: 342,425

[22] Filed: Jan. 25, 1982

[30] Foreign Application Priority Data

Jan. 26, 1981 [JP] Japan ................................. 56-9933

[51] Int. Cl.³ .............................................. F21V 7/04
[52] U.S. Cl. ....................................... 362/32; 128/6; 350/96.26
[58] Field of Search ................... 128/4, 6, 7, 8, 9, 10, 128/11, 22, 23; 362/32, 241, 247, 355, 804; 350/96.19, 96.2, 96.22, 96.26, 96.3, 319

[56] References Cited

U.S. PATENT DOCUMENTS 4,017,150  4/1977  Imai ................................. 350/96.18

Primary Examiner—Kyle L. Howell
Assistant Examiner—Max F. Hindenburg
Attorney, Agent, or Firm—Cushman, Darby & Cushman

[57] ABSTRACT

An illuminating system for endoscopes wherein, in order that a very wide range of the field of view of an observing system may be uniformly illuminated, a light guide and a bar-shaped reflector are so arranged that the optical axis of at least one of the light guide and bar-shaped reflector may not intersect at right angles with at least one of the exit end face of the light guide and entrance end face of the bar-shaped reflector. This illuminating system is easy to manufacture and has no loss of the light amount.

9 Claims, 45 Drawing Figures

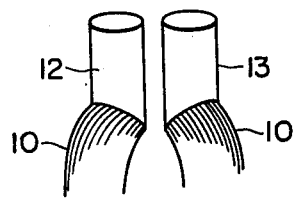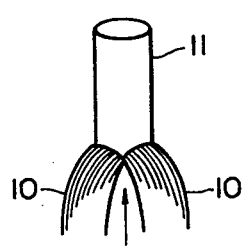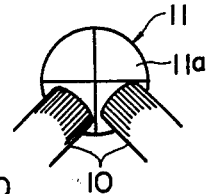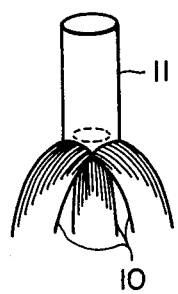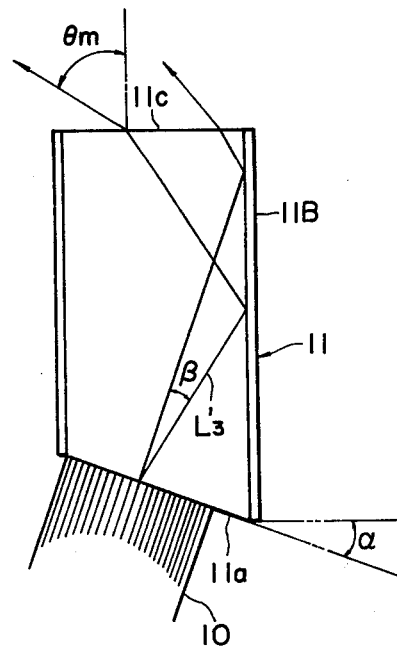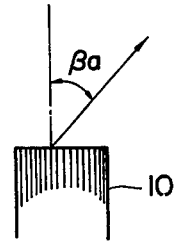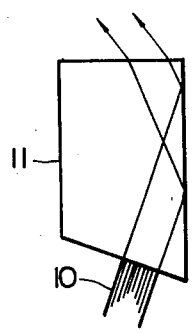

ILLUMINATING SYSTEM FOR ENDOSCOPES

BACKGROUND OF THE INVENTION (a) Field of the Invention

This invention relates to illuminating systems for endoscopes and more particularly to an illuminating system applicable to an endoscope of a wide angle of view.

(b) Description of the Invention

A conventional illuminating system for endoscopes is formed of an optical system 3 consisting of a light guide 3a and concave lens 3b arranged adjacently to each other in parallel with an observing optical system 2 within a tubular body 1 as shown in FIG. 1. However, as the angle of view of endoscopes has come to increase to be larger than 100 degrees, with such conventional illuminating system as is shown in FIG. 1, it has become difficult to well brightly illuminate the observable range of the endoscope to the peripheral side, because, if the power of the concave lens 3b is increased to brightly illuminate the range to the peripheral side, as shown in FIG. 2, such rays of light as the totally reflecting ray $L_1$ and the ray $L_2$ hitting the side of the concave lens 3b will increase and the light amount will be lost. Further, in order to prevent the light from hitting the side of the concave lens, the diameter of the concave lens must be made larger. This is not desirable. In order to eliminate such defects of the conventional illuminating system for endoscopes, as shown in FIG. 3, it is suggested to diagonally cut the exit end face of a light guide 4 and expand the illuminated range by utilizing the refraction of the light on this face. However, in this method, if the angle made by the exit end face 4a of the light guide 4 with the axis 4b of the light guide is made smaller to expand the illuminated range, as shown in FIG. 4, the light will be totally reflected on the exit end face 4a and the light amount loss will be caused. As clear from FIG. 3, it is impossible in principle to expand the range to be illuminated to be larger than 2p. For such reasons, in fact, the illuminating system of such formation as is shown in FIG. 3 can not be used for endoscopes having an angle of view larger than 120 degrees.

SUMMARY OF THE INVENTION

Therefore, a primary object of the present invention is to provide an illuminating system for endoscopes whereby a very wide range can be illuminated in spite of a simple formation.

According to the present invention, this object is attained by arranging the optical axis of at least one of a light guide consisting of a light transmitting fiber bundle and a bar-shaped reflector arranged in front of the light guide so as not to intersect at right angles with at least one of the exit end face of the light guide and the entrance face of the bar-shaped reflector.

According to a preferred formation of the present invention, the bar-shaped reflector has an entrance end face consisting of at least one flat face or curved face intersecting diagonally with its optical axis. The bar-shaped reflector is made preferably of a single fiber so as not only to be easy to make but also to have no light loss and to be able to uniformly illuminate the entire range.

According to another preferred formation of the present invention, the bar-shaped reflector has a reflecting face diagonally intersecting with its optical axis. Further, the bar-shaped reflector may have both end faces intersecting at right angles with its optical axis.

BRIEF DESCRIPTION OF THE DRAWINGS

FIGS. 9 to 11 are views each showing a modification of the embodiment shown in FIG. 5;

FIG. 12 is a further magnified view of FIG. 6;

FIG. 13 is a view showing the light coming out of the light guide into air;

FIG. 14 is a view showing another modification of the embodiment shown in FIG. 5;

DESCRIPTION OF THE PREFERRED EMBODIMENTS

Figure 5:
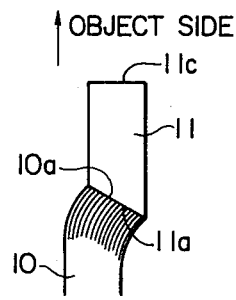
FIG. 5 is a view showing an embodiment of an illuminating system according to the present invention.

The detailed contents of the illuminating system of the present invention shall be explained in the following on the basis of the respective embodiments. FIG. 5 shows an embodiment of the present invention in which a bar-shaped reflector 11 having the entrance end face 11a cut diagonally is arranged in front of a light guide 10a, that is, the exit end face 10a of the light guide 10 and the entrance end face 11a of the bar-shaped reflector 11 are formed to intersect diagonally instead of at right angles with the center axis 11b of the bar-shaped reflector 11. The bar-shaped reflector 11 is considered to be of a glass bar, single fiber, metal pipe smooth on the inside surface and glass bar plated on the side surface. However, the single fiber is superior in respect that the reflection factor of the reflecting face is high, that, even if the reflecting face is stained in the assembling process, the reflection factor will not be reduced and that the cost is low.

Figure 6:
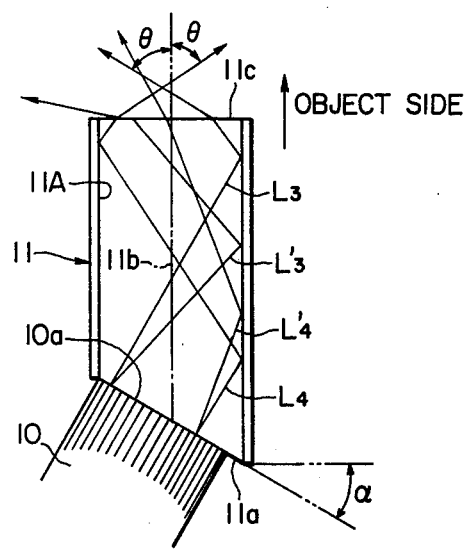
FIG. 6 is a view showing the progress of the light in the embodiment of the present invention.
Figure 7:
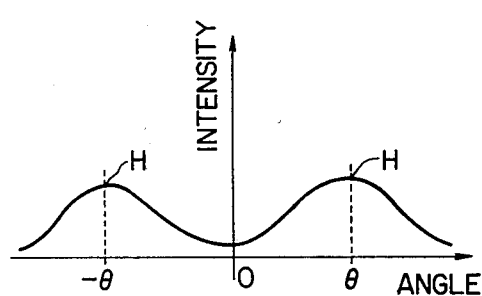
FIGS. 7 and 8 are views each showing the distribution of the light in the embodiment of the present invention.
Figure 8:
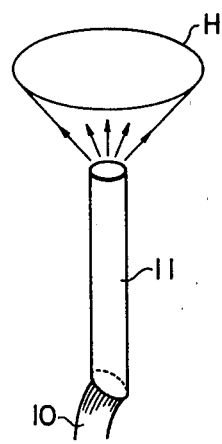

FIG. 6 is a magnified view of the above mentioned embodiment in which a single fiber having the entrance end face cut diagonally is used for the bar-shaped reflector 11 as sectioned in the plane (referred to as the meridional plane hereinafter) including its center axis 11b and the maximum inclination direction of the entrance end face 11a. The rays parallel with the axes of the fibers among the rays coming out of the respective fibers of the light guide 10 have the maximum intensity. Now, two rays $L_3$ and $L_4$ of light parallel with the axes of such fibers shall be considered. As shown in FIG. 6, the ray $L_3$ reflects once on the side surface of the single fiber 11, is then refracted on the exit end face, comes out of the fiber 11 and advances in the direction of the angle $\theta$ made with the center axis 11b of the single fiber. Also, the ray $L_4$ reflects twice on the side surface of the single fiber 11 and then advances rightward in the direction of the angle $\theta$ made with the center axis 11b. Further, the rays $L'_3$ and $L'_4$ which are not paralleled with the center axis 11b of the light guide 11 reflect on the side surface of the single fiber 11 in the same manner, are refracted on the exit end face 11c and expand toward the object. Therefore, the light distributing characteristic by the illuminating system shown in FIG. 8 is of such form having rises H in the direction of the angle of $\pm\theta$ with the center axis 11b of the single fiber 11 as is shown in FIG. 6. If the angle of inclination of the entrance end 11a of the single fiber is represented by $\alpha$ and the refractive index of the core 11A of the single fiber 11 is represented by $n_c$, the above mentioned angle $\theta$ will be given by the following formula (1):

$$\theta = \sin^{-1}(n_c \sin \alpha) \tag{1}$$

Therefore, for example, if $\alpha=32°$ and $n_c=1.8$, $\theta$ will be $\theta=72°53'$. Thus, even with an endoscope of a wide angle of view exceeding 140 degrees, the field of view can be well brightly illuminated to the peripheral side. By the way, the drop of the light amount in the central part can be eliminated by adding another illuminating system. That is, if another illuminating system applicable to an endoscope of a normal angle of view is added to the illuminating system according to the present invention to illuminate the central part of the field of view, it will be possible to illuminate from the peripheral part to the central part over a super-wide angle of view since the central part of the field of view is illuminated by the another illuminating system. Further, if $\alpha \geq \sin^{-1}(1/n_c)$, the rays $L_3$ and $L_4$ will be totally reflected on the exit end face 11c of the single fiber 11. It is not desirable. As is described later, in practice, as $n_c \geq 1.68$, $\alpha < 36.5°$ is preferable.

The above explanation has been made on the light proceeding within the meridional plane. As regards the expansion of the light proceeding within the plane vertical to the meridional plane, as already known as the characteristic of the fiber, when the length of the bar-shaped reflector is large enough, the light will uniformly expand in response to the shape of the exit end face 11c. Therefore, as in FIG. 8, there will a circular part H of the maximum light amount. Further, in order that the light distribution may be substantially uniform, as described later, it is preferable that the number M of reflections on the side surface of the bar-shaped reflector 11 of the ray proceeding within the meridional plane of the light guide 10 is at least 1. Further, in case a long bar-shaped reflector can not be used, as shown in FIG. 9, two bar-shaped reflectors 12 and 13 may be so arranged that their meridional planes may intersect at right angles with each other. As modifications of this FIG. 9, as seen in FIGS. 10 and 11 (FIG. 10B, is a view of FIG. 10A as seen in the direction indicated by the arrow), the entrance end face 11a of the single fiber 11 is ground to be pyramidal, a plurality of the ground faces are made respective entrance faces and the light guides 10 may be arranged on the respective entrance faces. If the light guides are arranged as shown in FIGS. 9 to 11, even if the length of the bar-shaped reflector 11 is small, a uniform illumination will be able to be made. Even in the case of these embodiments, it is desirable that the bar-shaped reflector 11 is of such length that there are rays reflecting at least once on the side surface of the bar-shaped reflector 11 among the exit rays coming out of the light guides 10 and proceeding respectively within the meridional planes of the bar-shaped reflector 11 in parallel with the axes of the light guides 10.

In the above, it has been qualitatively explained that, with the illuminating system according to the present invention, a wide angle illumination is possible. Now, the relations between the angle of inclination $\alpha$, diameter d and length L of the entrance end face 11a of the bar-shaped reflector 11 and the angle of view $2\omega$ of the endoscope in the case of using the illuminating system for a practical endoscope shall be described in the following. In FIG. 12 (showing FIG. 6 as further magnified), if the ray in which the angle made with the axis of the light guide 10 is maximum among the rays entering the single fiber from the light guide 10 is represented by $L'_3$ and the angle made by the ray $L'_3$ with the axis of the light guide 10 is represented by $\beta$, the following relation will hold:

$$\sin \beta = (1/n_c) \sin \beta a \tag{2}$$

where $\beta a$ represents an angle made with the axis of the light guide by the ray having the maximum angle with the axis of the light guide 10 among the rays coming out of the light guide 10 into air as shown in FIG. 13. Within the meridional plane in the optical system shown in FIG. 12, the ray $L'_3$ has the maximum refraction angle $\theta m$ after being refracted on the exit end face 11c of the single fiber 11. If the angle of view of the endoscope is $2\omega$, in order that the illumination may cover the entire field of view, $\theta m$ must be $\theta m \geq \omega$. As $\theta m$ is given by the following formula (3), in the optical system shown in FIG. 12, the below mentioned formula (4) must be satisfied:

$$\theta m = \sin^{-1} \{n_c \sin (\alpha + \beta)\} \tag{3}$$

$$\sin^{-1} \{n_c \sin (\alpha + \beta)\} \geq \omega \tag{4}$$

If the refractive index of the clad 11B of the single fiber 11 is represented by $n_R$, in order that the ray coming at the angle $\delta$ out of the single fiber may be totally reflected, the following formula (5) must be satisfied:

$$\sqrt{n_c^2 - n_R^2} \geq \sin \omega \tag{5}$$

As $n_R \approx 1.5$ and $\omega \geq 50°$ in practice, $n_c \geq 1.68$ is preferable.

Now, the position of the light guide 10 placed at the entrance end 11a of the single fiber shall be considered. In case the light guide 10 is thinner than the bar-shaped reflector (single fiber) 11, in such position relation as is shown, for example, in FIG. 14, the rays within the meridional plane parallel with the axis of the light guide will be all reflected leftward to cause the illumination to fluctuate. This will occur in case the numbers of reflections on the side surface of the single fiber of the rays parallel with the axis of the light guides among the rays coming out of the respective fibers of the light guide are all the same. In the case of the optical system shown in FIG. 6, as the number of reflections of the ray $L_3$ is one and the number of reflections of the ray $L_4$ is 2, no illumination fluctuation will be caused. Thus, in order that no remarkable illumination fluctuation may be caused, it is a condition that the numbers of reflections of the rays paralled with the axis of the light guide 10 should not be the same at all. The number M of reflections of the ray parallel with the axis of the light guide 10 and coming in through any point Q (FIG. 15) of the entrance end 11a of the single fiber is given by the following formula (6):

$$M = \left[ \frac{\left\{ L + \left( \frac{X_0}{\sin \alpha} \right) + X_0 \tan \alpha \right\} \tan \alpha + \frac{d}{2}}{d} \right] \text{gauss} \tag{6}$$

where d means a diameter of the single fiber, $X_0$ means an X coordinate of the entering point Q, L means a length of the center axis 11b of the single fiber and [ ] gauss means a maximum integer not exceeding the value in the parentheses. Further, the manner of taking the coordinate system is as in FIG. 15. M in the formula (6) varies with the value of $X_0$ but, when $X_0$ moves from the left to the right on the exit end face 10a of the light guide, that is, when $X_0$ varies from Xm to XM, unless the value of the number M of reflections varies, a remarkable illumination fluctuation will be caused. In the above, Xm means an X coordinate of the left end of the exit end face 10a of the light guide 10 and XM means an X coordinate of the right end.

Therefore, it is desirable to select the values of L, d, Xm, XM and $\alpha$ so that, when $X_0$ is varied, the value of M will vary at least by 1.

When the respective values are so selected that, as in the above, when the formulas (4) and (5) are satisfied and $X_0$ is varied in the formula (6), M will vary at least by 1, an illuminating system having little illumination fluctuation over a wide field of view will be obtained. By the way, in case the barshaped reflector 11 is a hollow inside surface reflector (for example, of a metal pipe plated on the inside surface), $n_c$ will be $n_c = 1.0$ and the formula (5) need not be considered.

The parallax between the illuminating system 3 and observing system 2 can be eliminated by utilizing the above described relation between the number M of reflections and the illumination fluctuation.

Figure 16:
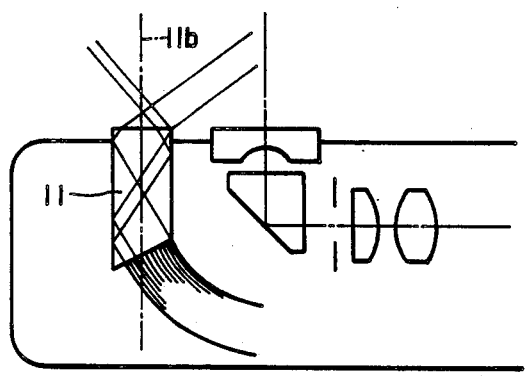
FIG. 16 is a view showing an embodiment in which an illuminating system according to the present invention is used for a side view type endoscope.

FIG. 16 relates to a side view type endoscope and shows an example of an illuminating system in which the parallax is eliminated by utilizing the optical system of the present invention. If L, d, Xm, XM and $\alpha$ are properly selected on the basis of the above described relation between to bar-shaped reflector 11 and the light guide 10, the light amount going rightward of the optical axis 11b of the single fiber in FIG. 16 will be able to be made larger than the light amount going leftward and a uniform illumination having the parallax eliminated will be able to be made.

Figure 17A:
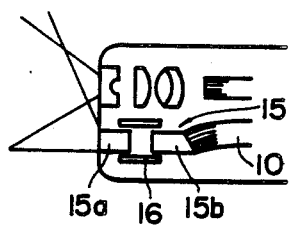
FIGS. 17a and 17b are views showing an embodiment in which the illuminating direction is made variable.
Figure 17B:
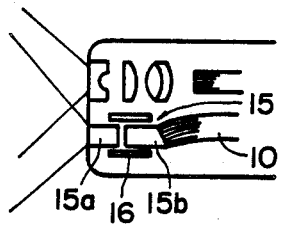

FIG. 17 shows another embodiment of an illuminating system in which the parallax is eliminated by applying the principle of the present invention. That is to say, a single fiber 15 is divided into two parts 15a and 15b, both parts are connected with each other through a hollow inside surface reflector 16 (for example, of a metal pipe plated on the inside surface), the part 15a is fixed and the part 15b is moved so that the distance between both parts of the single fiber 15 may be adjusted, for example, the state shown in FIG. 17A may be varied to the state shown in FIG. 17B. The variation of the distance between both single fiber parts 15a and 15b corresponds to varying L in the formula (6). Therefore, as the number M of reflections varies, the illuminating direction will be thereby varied and the illuminated range will vary from the illumination adapted to the far point to the illumination in the diagonal direction adapted to the near point. Therefore, an illumination in which the object distance is from the infinite to the near point and a favorable observation most adapted to the object distance and having the parallax eliminated is possible can be made.

Further, even in case the light guide 10 and single fiber 11 are relatively moved along the surface of contact of the exit end 10a of the light guide 10 with the entrance end 11a of the single fiber 11 in the illuminating system of the formation shown in FIG. 6, the illuminating direction will be able to be varied and the same effect as of the method in FIG. 17 will be able to be obtained.

Figure 1:
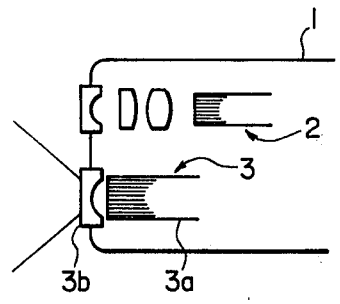
FIG. 1 is a view showing a formation of an endoscope provided with a conventional illuminating system.
Figure 2:
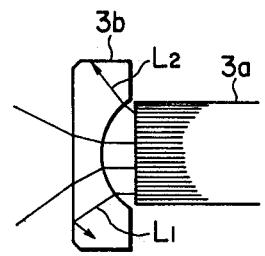
FIGS. 2 and 3 are views showing formations of respective conventional illuminating systems for endoscopes.
Figure 3:
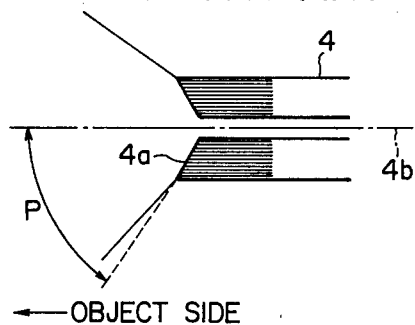
Figure 4:
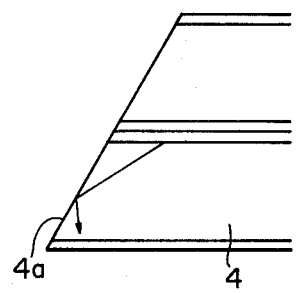
FIG. 4 is a magnified view of a part of FIG. 3.

In the above explained illuminating system of the present invention, as such concave lens 3b of a diameter larger than the diameter of the light guide 3a as is shown in FIG. 2 is not used, the range to be illuminated can be expanded without increasing the diameter of the exit end of the illuminating system.

Figure 15:
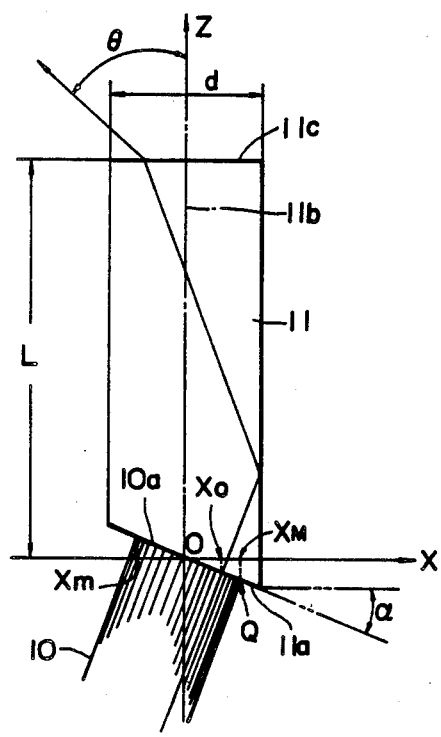
FIG. 15 is a view showing the relation between the shape and size of a bar-shaped reflector and the reflection of the light.

Examples of numerical values of the formation shown in FIG. 15 shall be given in the following:

| | | |
|---|---|---|
| d = 2.5 mm., | L = 6.25, | $\alpha$ = 30°, |
| $n_c$ = 1.85, | $\theta$ = 67°7', | |
| M = 1 when Xm = −0.75 and | | |
| M = 2 when XM = 0.75. | | |

In the above, the contents of the present invention have been described in detail on the basis of one embodiment. Further, various modifications shall be described.

Figure 18:
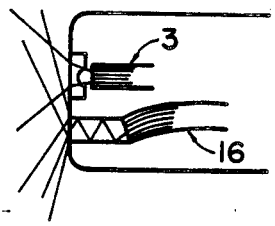
FIG. 18 is a view showing an embodiment in which an illuminating system according to the present invention and a conventional illuminating system are used as combined.

Shown in FIG. 18 is a combination of a conventional illuminating system 3 and an illuminating system of the present invention as used. Thereby, an illumination of a wide range can be made and the lack of the light amount in the direction of the front surface of the endoscope can be compensated.

Figures 19A, 19B, 19C:
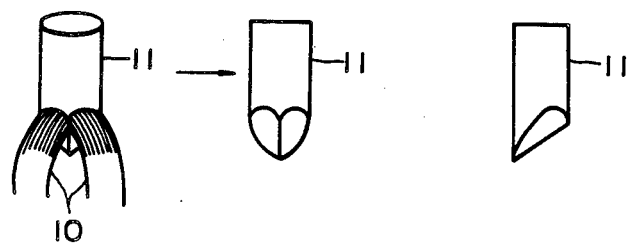
FIGS. 19a–c are views showing a modification of the bar-shaped reflector.

Further, FIG. 19 shows a modification in which the entrance end face 11a of a single fiber 11 is ground to be drill tip-shaped, FIG. 19A is an elevation showing the entire illuminating system consisting of two light guides 10 and single fiber 11, FIG. 19B is an elevation of only the single fiber 11 and FIG. 19C is a side view of the single fiber 11 as seen in the direction indicated by the arrow in FIG. 19B.

Figure 20:
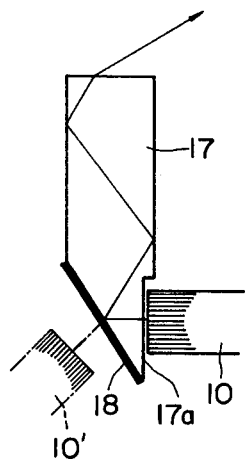
FIGS. 20 to 22 are views each showing an embodiment of an illuminating system according to the present invention as formed to be adapted to side view type endoscopes.

FIG. 20 is of an embodiment in which the illuminating system of the present invention is applied to a side view type endoscope. That is to say, a single fiber 17 is diagonally ground at one end, a reflecting film 18 is provided on this ground surface, a part of the side surface of the single fiber is ground to be an entrance face 17a and a light guide 10 is arranged so as to oppose the exit of the light guide to the entrance face 17. By the way, the side surface may be an unground cylindrical surface as it is and, if the light is totally reflected on the part to be provided with the reflecting film, this reflecting film 18 need not be present in the formation. In this embodiment, it is necessary that the angle of inclination of the reflecting face should be such that the ray parallel with the center axis of the light guide 10 and reflected by this reflecting face 18 may not be parallel with the axis of the single fiber 17. In case the angle of inclination is made so, the ray parallel with the optical axis of the light guide 17 will be just the same as coming in the direction of a light guide 10' illustrated by chain lines in FIG. 20, therefore, the formation will be the same as of the illuminating system shown in FIG. 6 and a wide range in the side view direction will be able to be illuminated.

Figure 21:
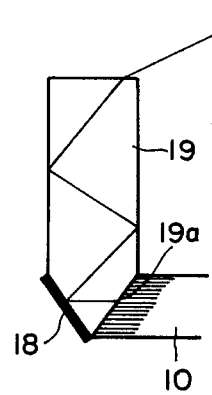

Shown in FIG. 21 is a modification of the embodiment shown in FIG. 20 in which the entrance end face 19a of a single fiber 19 is inclined.

Figure 22:
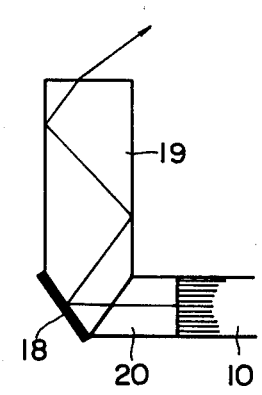

Shown in FIG. 22 is that two single fibers 19 and 20 formed diagonally on the end surfaces are jointed with each other on the end surfaces.

Figure 23:
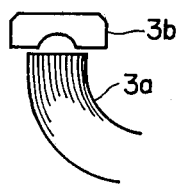
FIG. 23 is a view showing a conventional illuminating system for side view type endoscopes.

Shown in FIG. 23 is an illuminating system used for a conventional example, the light amount is lost by 20 to 40% in the bent portion of the light guide. However, in the case of the embodiments shown in FIGS. 20 to 22, the light guide 10 is not bent and therefore there is no loss of the light amount.

Figure 24:
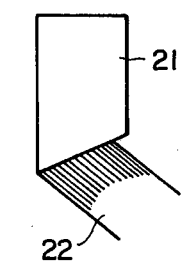
FIG. 24 is a view showing an embodiment in which the entrance end face of a light guide is also inclined.

Shown in FIG. 24 is an arrangement of a single fiber 21 formed diagonally on the entrance end face and a light guide 22 formed diagonally on the exit end face.

Figure 25:
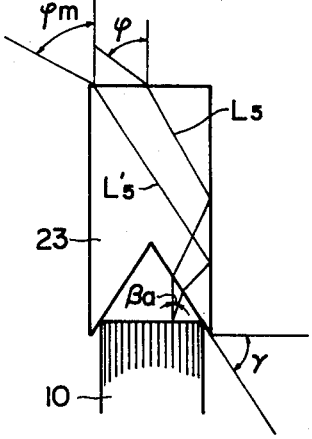
FIGS. 25 to 29 are views each showing another modification of a bar-shaped reflector having a V-shaped end face.

FIG. 25 is of an arrangement of a light guide 10 in the rear of a single bar 23 formed to be V-shaped on the entrance end face. In this embodiment, if the angle made by the entrance end face of the single fiber 23 with the exit end face of the light guide 10 is represented by $\gamma$, the exit angle of the ray $L_5$ parallel with the axis of the light guide 10 is represented by $\phi$ and the refractive index of the single fiber core is represented by $n_c$, $\phi$ will be given by the following formula (7):

$$\phi = \sin^{-1}\left[n_c \sin\{\gamma - \sin^{-1}(\sin \gamma / n_c)\}\right] \quad (7)$$

If the exit angle of the ray $L'_5$ coming out with the largest angle among the rays coming out of the light guide 10 into air is represented by $\beta a$, within the meridional plane of the single fiber 23, the light $\phi m$ of this ray refracted on the exit end face of the single fiber and coming out toward the object will be given by the following formula (8):

$$\phi m = \sin^{-1}\left[n_c \sin\left(\gamma - \sin^{-1}\left(\frac{\sin(\gamma - \beta a)}{n_c}\right)\right)\right] \quad (8)$$

If the angle of view of the endoscope is $2\delta$, in order to illuminate the entire field of view, $\phi m$ must be $\phi m \geq \omega$. Further, in order that the light may be totally reflected on the single fiber, the condition shown by the formula (5) must be satisfied. Therefore, in the case of the embodiment shown in FIG. 25, when $\gamma = 60°$ and $n_c = 1.8$, $\phi$ will be $\phi = 69°$ and therefore, even with the endoscope of an angle of view more than 140 degrees, the illumination will be possible.

Figure 26:
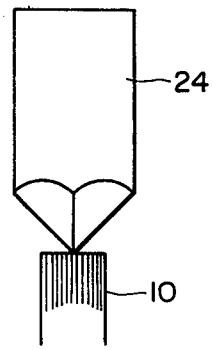

Shown in FIG. 26 is a modification of the embodiment shown in FIG. 25 in which the entrance end face of a single fiber 24 is formed to be square pyramidal. This embodiment is substantially the same in the operation and effect as the embodiment shown in FIG. 25 but has an advantage that the end face is easy to grind. By the way, the shape of the end face may be conical or conically nonspherical and the V-shaped part may not be a flat surface but may be a curved surface like a columnar surface. In the embodiments shown in FIGS. 25 and 26, a part and the other part of the rays coming out the light guides 10 need not be different in the number of reflections within the bar-shaped reflections 23 and 24. That is to say, as the light pencils entering the bar-shaped reflectors 23 and 24 come out of the bar-shaped reflectors while expanding symmetrically, the light will be distributed uniformly to the right and left.

Figure 27:
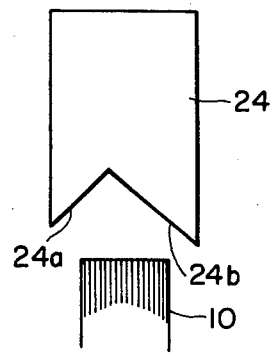
Figure 28:
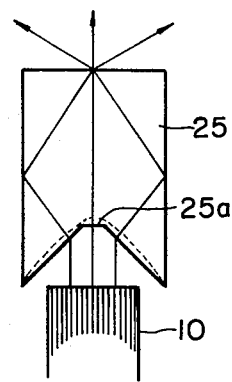
Figure 29:
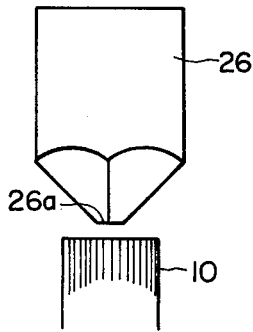
Figure 30:
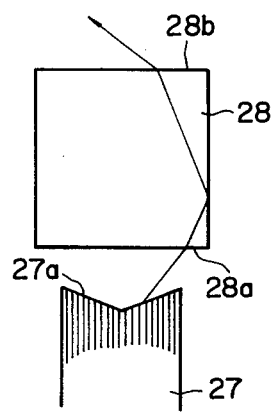
FIG. 30 is a view showing an embodiment in which the exit end face of a light guide is V-shaped.

FIGS. 27 to 30 are of modifications of either FIG. 25 or FIG. 26. FIG. 27 is of a modification in which the V-shaped ground face of the single fiber 24 is made asymmetrical (the face 24a is shorter than the face 24b) so that a larger amount of light may be distributed to only one side of the right and left. Further, in FIGS. 28 and 29, faces 25a and 26a are provided respectively at right angles with the optical axes of the light guides 10 in the centers of the bar-shaped reflectors 25 and 26 so that the lights may pass through them and the lack of the light amount in the center may be eliminated. By the way, even if these faces 25a, 26a and the V-shaped part are made curved faces as shown by dotted lines in FIG. 28, the same effects will be obtained. Further, shown in FIG. 30 is that the entrance end face 28a and exit end face 28b of a single fiber 28 are made parallel with each other (vertical to the axis of the single fiber) and the exit end face 27a of a light guide 27 is V-shaped. By thus selecting the shape of the exit end face 27a of the light guide 27 to be of any shape, the same operations and effects as of the embodiments shown in FIGS. 27 to 29 can be obtained.

Figure 31:
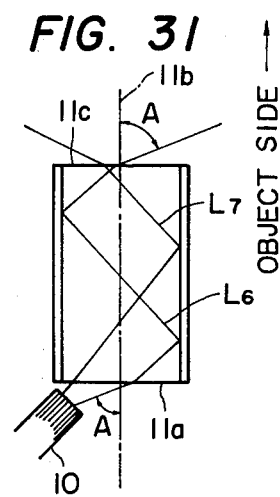
FIGS. 31 to 34 are views each showing an embodiment in which the exit end face of a light guide is arranged as inclined to the axis of a bar-shaped reflector.
Figure 35:
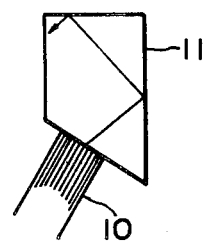
FIG. 35 is a view showing a total reflection on the exit end face of the embodiment shown in FIG. 6.

In the embodiment shown in FIG. 31, both of the entrance end face 11a and exit end face 11c of the bar-shaped reflector 11 are made faces vertical to its axis and the light guide 10 is so arranged that its optical axis may be diagonal to the axis 11b of the bar-shaped reflector 11. According to this embodiment, the light coming in at an angle A to the axis 11b of the bar-shaped reflector 11 comes out of the bar-shaped reflector 11 at the same angle A. Therefore, even when a single fiber or the like is used for the bar-shaped reflector 11, the light will never be prevented by the total reflection from coming out on the object side. For example, as shown in FIG. 35, in the case of such illuminating system as is shown in FIG. 6, the light coming in at a very large angle to the axis of the single fiber will be totally reflected on the exit face.

Further, in the embodiment shown in FIG. 31, among the rays coming out of the light guide 10 parallelly with the axis of the light guide 10 and proceeding within the meridional plane of the bar-shaped reflector 11, the ray, for example, $L_6$ reflected by an even number of times on the side surface of the bar-shaped reflector 11 and then coming out of the bar-shaped reflector 11 is directed rightward and, on the other hand, the ray, for example, $L_7$ reflected by an odd number of times and then coming out is directed leftward and therefore the light distribution can be uniformed. The other rays are also uniformed by the reflections by the bar-shaped reflector 11. The longer the bar-shaped reflector 11, the more symmetrical the light distribution of the illuminating system with respect to the axis of the bar-shaped reflector.

Figure 32:
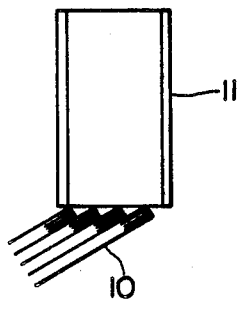
Figure 33:
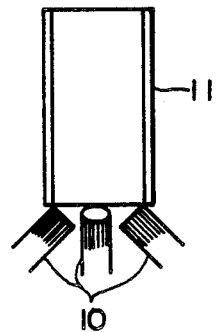
Figure 34:
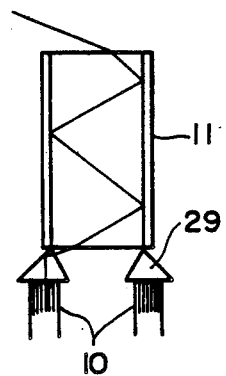

FIGS. 32 to 34 are of modifications of the embodiment shown in FIG. 31. FIG. 32 is of many light guides 10 arranged in steps. FIG. 33 is of a plurality of light guides 10 arranged in different directions. FIG. 34 shows that the light out of the light guide is made to come in the direction inclined to the axis into the bar-shaped reflector 11 through a prism 29. The embodiments shown in FIGS. 32 to 34 are substantially the same in the operations and effects as the embodiment in FIG. 31. However, with the same diameter of the single fiber, the rays from more light guides than in the embodiment in FIG. 31 can be transmitted in the embodiments in FIGS. 32 to 34. Further, in the embodiments in FIGS. 33 and 34, the rays from a plurality of light guides are made to come in respectively different directions into the single fibers. Therefore, they are superior in respect that the light distribution can be made more uniform than in the embodiment in FIG. 31.

Figure 36:
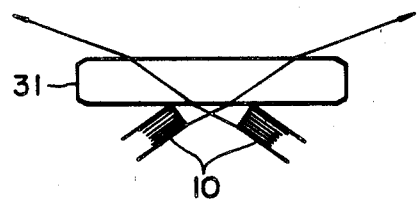
FIG. 36 is a view showing an example in which an illumination is made through a glass cover.

Further, in case a single fiber is used for the bar-shaped reflector in each of the above embodiments, it will be able to be also a glass cover. In case an ordinary glass plate is used for the glass cover, in order to prevent the loss of light, unless such large glass cover 31 as in FIG. 36 is used, the angle of view will not be able to be made wide and the light distribution will not be able to be uniformed.

Figure 37:
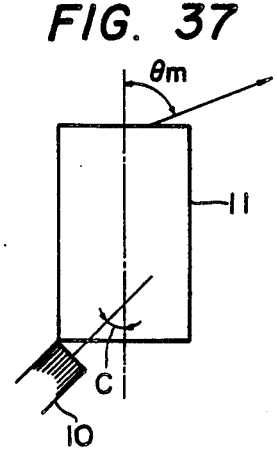
FIG. 37 is a view for explaining the relation between the bar-shaped reflector and the light in the embodiment shown in FIG. 31.

Now, the embodiments in FIGS. 31 to 34 shall be more particularly explained in the following. As shown in FIG. 37, if the angle made by the axis of the light guide 10 with the axis of the bar-shaped reflector 11 is represented by C and the angle made by the ray of the maximum exit angle among the rays coming out of the bar-shaped reflector 11 with the optical axis of the reflector is represented by $\theta m$, the following formula (9) will hold:

$$\theta m = C + \beta a \quad (9)$$

As $\theta m$ must be $\theta m \geq \omega$, it is preferable that c satisfies the following formula (10):

$$C \geq \omega - \beta a \quad (10)$$

Figure 39:
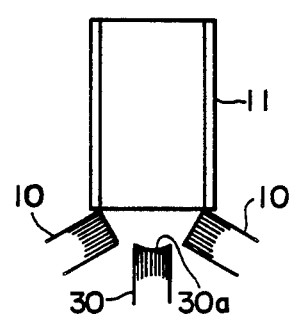
FIG. 39 is a view showing an embodiment in which a light guide along the optical axis of a bar-shaped reflector is added.
Figure 38:
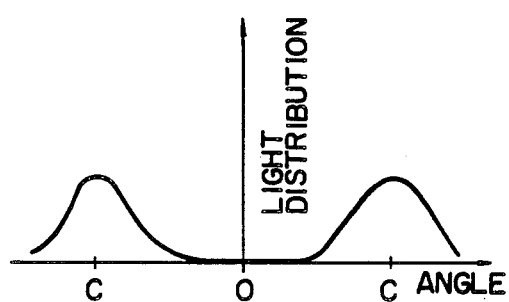
FIG. 38 is a view showing the distribution of the light in the illuminating system in FIG. 37.
Figure 40:
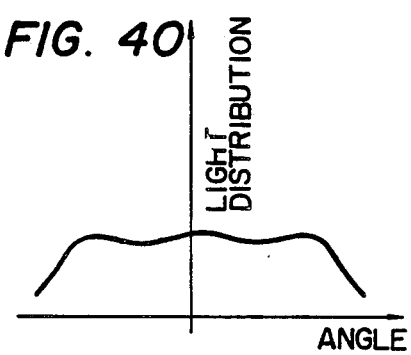
FIG. 40 is a view showing the distribution of the light in the embodiment shown in FIG. 39.

In case the endoscope is used in practice, $\beta a$ will be 35° at most, $\omega$ will be more than 50° and therefore C will be more than 15°. In the embodiments in FIGS. 31 to 34, in case C is larger than $\beta a$, the light will not reach the vicinity of the center of the field of view and the light distribution will be as shown in FIG. 38. In such case, as described above, the light guides 10 may be used as combined with a light guide illuminating the vicinity of the center of the field of view. FIG. 39 is of an example of such combination in which a light guide 30a having the exit end face 30a formed to be a concave face is arranged on the axis of the single fiber 11. The light distribution in this example is as shown in FIG. 40 and is found to be remarkably improved as compared with FIG. 38.

Figure 41:
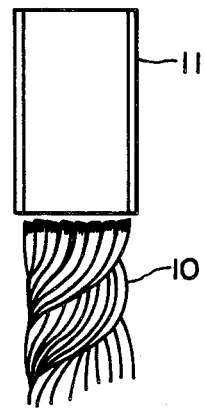
FIG. 41 is a view of an embodiment in which the light guide is made spiral.

In the embodiment shown in FIG. 41, a light guide 10 formed by spirally twisting fibers is placed at the entrance end of a single fiber 11. In the case of this embodiment, if the axes of the fibers forming the light guide 10 are considered as the axes of the light guides in the other embodiments, the operations and effects will be able to be understood to be the same as are already explained. That is to say, according to this arrangement, as each end face of the spirally twisted fibers is obliqued in various directions to the optical axis of the single fiber 11, the light distribution will become more uniform. Further, if the slender fibers are bundled in an appropriate manner, the illuminating system illustrating the vicinity of the center of the field of view will not be required.

I claim:

1. An illuminating system for endoscopes comprising a light guide means formed of a light transmitting fiber bundle and a bar-shaped reflecting means arranged in front of said light guide means, said light guide means and bar-shaped reflecting means being so arranged that the optical axis of at least one of said light guide means and bar-shaped reflecting means do not intersect at right angles with at least one of the exit end face of said light guide means and the entrance end face of said bar-shaped reflecting means.

2. An illuminating system for endoscopes according to claim 1 wherein said bar-shaped reflecting means has an entrance end face including at least one flat face intersecting diagonally with its axis.

3. An illuminating system for endoscopes according to claim 1 wherein said bar-shaped reflecting means has an entrance end face including at least one curved face intersecting diagonally with its axis.

4. An illuminating system for endoscopes according to claim 1 or 2 wherein said bar-shaped reflecting means includes a reflecting face intersecting diagonally with its axis.

5. An illuminating system for endoscopes according to claim 1 wherein said bar-shaped reflecting means has both end faces intersecting at right angles with its axis.

6. An illuminating system for endoscopes according to claims 1 or 2 wherein said bar-shaped reflecting means is a single fiber.

7. An illuminating system for endoscopes according to claims 1 or 2 wherein said light guide means consists of a plurality of light guide elements.

8. An illuminating system for endoscopes according to claim 1 wherein the distance between the entrance end face and final exit and face of said bar-shaped reflecting means is variable.

9. An illuminating system for endoscopes according to claim 1 further comprising an another illuminating system including a light guide and a lens system disposed in front of said light guide.

* * * * *